United States Patent [19]

Avar

[11] Patent Number: 5,306,823
[45] Date of Patent: Apr. 26, 1994

[54] 2,2,6,6-TETRAALKYLPIPERIDINE COMPOUNDS USEFUL AS LIGHT STABILIZERS

[75] Inventor: Lajos Avar, Biel-Benken, Switzerland

[73] Assignee: Sandoz Ltd., Basel, Switzerland

[21] Appl. No.: 836,027

[22] Filed: Feb. 14, 1992

[30] Foreign Application Priority Data

Feb. 19, 1991 [GB] United Kingdom ............ 9103415

[51] Int. Cl.$^5$ ............ C07D 401/12; C07D 409/12; C08K 5/34
[52] U.S. Cl. ............ 546/224; 546/193; 546/202; 546/212; 524/99; 524/102; 524/103
[58] Field of Search ............ 546/193, 202, 212, 224

[56] References Cited

U.S. PATENT DOCUMENTS

| | | | |
|---|---|---|---|
| 4,730,017 | 3/1988 | Avar | 524/103 |
| 4,916,175 | 4/1990 | Avar | 546/18 |
| 5,017,702 | 5/1991 | Aumueller | 546/212 |

FOREIGN PATENT DOCUMENTS

| | | |
|---|---|---|
| 0389427 | 9/1990 | European Pat. Off. . |
| 0389434 | 9/1990 | European Pat. Off. . |
| 1492494 | 11/1977 | United Kingdom . |
| 2180537 | 4/1987 | United Kingdom . |
| 2197318 | 5/1988 | United Kingdom . |

OTHER PUBLICATIONS

Search Report (France) corresponding application FR 9201660 (1992).
Chemical Abstracts, vol. 113, p. 82 (1990): Abstract No. 25582.

*Primary Examiner*—C. Warren Ivy
*Assistant Examiner*—Celia Chang
*Attorney, Agent, or Firm*—Robert S. Honor; Richard E. Vila; Andrew N. Parfomak

[57] ABSTRACT

Novel compounds according to formula I

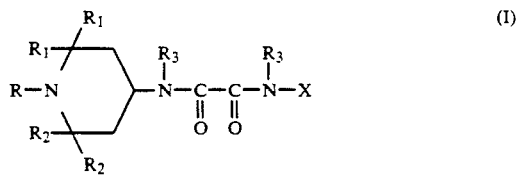

are disclosed, as well as processes for their production and methods for their use.

These compounds are useful as light stabilizers for polymeric materials, particularly in acid catalyzed stoving finishes such as those encountered in the top coat of two layer metallic finishes.

8 Claims, No Drawings

2,2,6,6-TETRAALKYLPIPERIDINE COMPOUNDS USEFUL AS LIGHT STABILIZERS

The invention relates to novel tetraalkylpiperidine compounds, suitable as light stabilisers in polymeric systems.

According to the invention there is provided a compound of formula

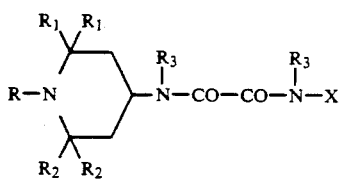
(I)

in which
R is hydrogen; oxygen; —OH; $C_{1-8}$alkyl; —O—$C_{1-8}$alkyl; —O—CO—$C_{1-8}$ alkyl; —O—CO—phenyl or —COR$_5$;
where
R$_5$ is —C(R$_3$)=CH$_2$, $C_{1-6}$alkyl, phenyl, —CO—phenyl, —NR$_7$R$_8$, —COC$_6$H$_5$, —CH$_2$—C$_6$H$_5$, —CO—OC$_{1-12}$alkyl or —COOH; R$_7$ is hydrogen, $C_{1-12}$ alkyl, $C_{5-6}$ cycloalkyl, phenyl, phenyl-$C_{1-4}$alkyl or $C_{1-12}$alkylphenyl and R$_8$ is $C_{1-12}$alkyl or hydrogen,
each R$_1$ independently, is —CH$_3$ or —CH$_2$($C_{1-4}$alkyl) or both groups R$_1$ together form a group —(CH$_2$)$_5$—;
each R$_2$, independently, is —CH$_3$ or —CH$_2$($C_{1-4}$alkyl) or both groups R$_2$ together from a group —(CH$_2$)$_5$—;
each R$_3$ independently, is hydrogen or $C_{1-4}$ alkyl; and
X is a group of formula α, β, γ or δ

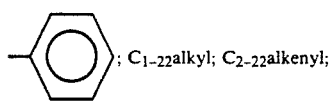
(α)

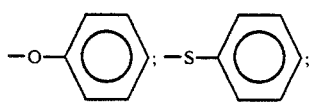
(β)

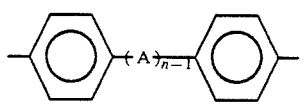
(γ)

(δ)

where
either R$_{10}$ is

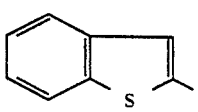
; $C_{1-22}$alkyl; $C_{2-22}$alkenyl;

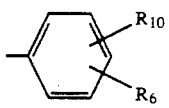

—N($C_{1-4}$alkyl)$_2$; —NH($C_{1-4}$alkyl) or halogen, and R$_6$ is hydrogen, halogen, $C_{1-8}$alkyl or $C_{2-8}$alkenyl
or
R$_{10}$ is $C_{1-22}$alkoxy and R$_6$ is hydrogen, $C_{1-8}$alkyl or $C_{1-8}$alkoxy, provided that when R$_{10}$ is alkoxy and R is acyl then R$_6$ is not hydrogen.
X$_1$ is

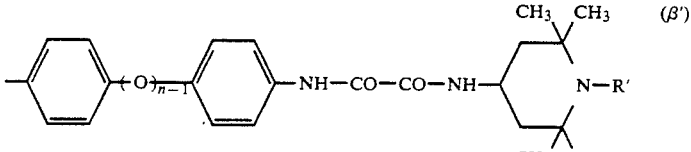

where
n is 1 or 2 and A is —S— or —O—.
Preferably R is R' where R' is hydrogen, $C_{1-4}$alkyl, O—$C_{1-4}$alkyl or —CO—R$_5$' where R$_5$' is —CH=C$_2$, $C_{1-4}$ alkyl or —CO—O—$C_{1-4}$ alkyl.
Preferably each R$_1$ and each R$_2$ is —CH$_3$.
Preferably R$_3$ is R$_3$' where R$_3$' is —CH$_3$ or hydrogen, more preferably R$_3$ is hydrogen.
Preferably X is a group of formula α or β, defined above.
X is more preferably X' where X' is a group of α' or β'.

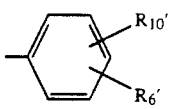
(α')

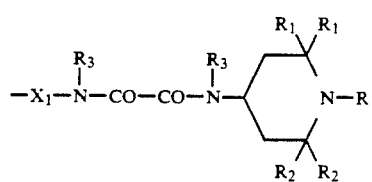
(β')

where either
R$_{10}$' is selected from $C_{1-4}$alkyl, $C_{2-4}$alkenyl, —N($C_{1-4}$alkyl)$_2$; —NH($C_{1-4}$alkyl) and phenyl; and R$_6$' is hydrogen or methyl or
R$_{10}$' is $C_{1-4}$alkoxy and R$_6$' is hydrogen, $C_{1-4}$alkyl or $C_{1-4}$alkoxy, provided that when R$_{10}$' is alkoxy and R is acyl then R$_6$' is not hydrogen.

Most preferably $R_{10}$ is $C_{1-4}$alkoxy (preferably ethoxy) and $R_6$ is hydrogen.

In this specification any $C_{1-12}$alkyl or $C_{1-6}$alkyl group is preferably a $C_{1-4}$alkyl group and any $C_{1-4}$alkyl group is preferably methyl or ethyl; preferably any alkoxy group is methoxy or ethoxy.

In this Specification, any group capable of being linear or branched is linear or branched.

Where a symbol appears more than once in a formula, its significances are independent of one another.

Further, according to the invention, there is provided a process for preparing a compound of formula I comprising reacting, at an elevated temperature,
i) 2 moles of a compound of formula II

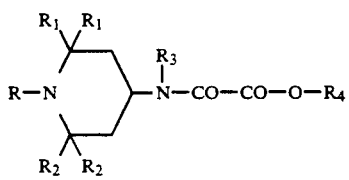

where $R_4$ is hydrogen, methyl or ethyl;
with 1 mole of a compound of formula III $$X_1-(NH-R_3)_2 \quad (III)$$

or ii) 1 mole of a compound of formula II with 1 mole of a compound of formula IIIa $$X-NH-R_3 \quad (IIIA)$$

where the symbols are as defined above.

Further according to the invention, there is provided a process for preparing a compound of formula I comprising reacting, at elevated temperature,
iii) 2 moles of a compound of formula IV

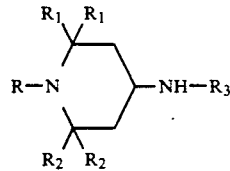

with 1 mole of a compound of formula V

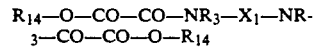

or iv) 1 mole of a compound of formula IV with 1 mole of a compound of formula Va

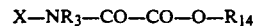

where $R_{14}$ is hydrogen, methyl or ethyl and the other symbols are as defined above.

Preferably in the process of the invention the temperature is in the range of 40° to 200° C.

Compounds of formula II to Va are known or may be made from known compounds by known methods.

Further, according to the invention there is provided a composition comprising a polymeric material and a compound of formula I defined above.

Further, according to the invention there is provided a method for stabilising a lacquer composition based on acrylic, alkyd or polyester resins (which, if desired can be crosslinked with melamine/formaldehyde resins, epoxide resins or polyisocyanates) which comprises incorporating into the resin one or more compounds of formula I as defined above.

The compound of formula I is used in an amount effective to improve the stability, especially the light stability of the material to which it is added.

Further, according to the invention there is provided a lacquer composition based on acrylic, alkyd and/or polyester resins (which if desired, can be crosslinked with melamine/formaldehyde resins, epoxide resins or polyisocyanates) containing one or more compounds of formula I as defined above.

The concentration of compound of formula I employed in the polymeric material is suitably 0.01 to 8% by weight, preferably 0.02% to 1% by weight and gives a clear improvement in the light- and weather stability of organic pigments in stoving finishes as well as reducing the tendency of such finishes to hairline cracking and loss of gloss as the result of weathering. This is also found for metallic finishes and excellent long-term stability of the clear top coat of two layer metallic finishes is obtained. In such finishes, the compound of formula I may be added to the metallic undercoat, the clear top coat or both, preferably only to the clear top coat. The metal surface to be finished may be under-coated with primer coatings as is customary in the art of coating metal surfaces.

The compound or compounds of formula I may be added before, during or after the polymerization step, and may be added in solid form; in solution, preferably as a liquid concentrate containing from 20 to 80% by weight of compound of formula I and 80–20% solvent; or as a solid masterbatch composition containing 10 to 80% by weight of compound of formula I and 90 to 20% by weight of a solid polymeric material which is identical with or compatible with the polymeric material to be stabilized.

Suitable polymeric materials include plastic materials for example polyethylene, polypropylene, ethylene/-propylene copolymers, polyvinyl chloride, polyester, polyamide, polyurethane, polyacrylonitrile, ABS, terpolymers of acrylates, styrene and acrylonitrile, styrene/acrylonitrile and styrene/butadiene. Other plastics materials such as polybutylene, polystyrene, chlorinated polyethylene, polycarbonate, polymethylmethacrylte, polyphenylene oxide, polypropylene oxide; polyacetals, phenol-formuladehyde resins and epoxy resins may also be used. Preferred plastic materials are polypropylene, polyethylene, ethylene/propylene copolymers and ABS. Natural polymers for example natural rubber may also be stabilized, as may lubricating oils containing polymeric material.

The compounds of formula I may be incorporated by known methods into the polymeric material to be stabilized. Of particular importance is blending of the compounds with thermoplastic polymers in the melt, for example in a melt blender or during the formation of shaped articles, including foils, films, tubes, containers, bottled, fibres and foams by extrusion, injection moulding, blow moulding, spinning or wire coating.

It is not essential for the polymeric material to be fully polymerised before mixing with the compounds according to the invention. The compounds may be mixed with monomer, prepolymer or precondensate, and the polymerisation or condensation reaction is carried out subsequently. This will of course be the preferred method of incorporation of the compounds into the thermosetting polymers, which cannot be melt blended.

Further antioxidants can be added to polymeric material either before, at the same time as or after (but before polymerisation occurs) the addition of a compound according to the invention.

Examples of antioxidants include benzofuran-2-ones, indolin-2-ones and sterically hindered phenols, sulphur- and phosphorus-containing compounds and mixtures thereof.

Preferred sterically hindered phenols include β-(4-hydroxy-3,5-ditert.butylphenyl)-propionyl stearate, methane tetrakis-(methylene-3 (3′,5′-ditert.butyl-4-hydroxy-phenyl)-propionate), 1,3,3-tris-(2-methyl-4-hydroxy-5-tert.butyl phenyl)butane, 1,3,5-tris (4-tert.butyl-3-hydroxy-2,6-di-methylbenzyl)-1,3,5-triazinyl-2,4,6 (1H, 3H, 5H)-trione, bis-(4-tert.butyl-3-hydroxy-2,6-di-methylbenzyl)dithiol terephthalate, tris (3,5-ditert.butyl-4-hydroxybenzyl) isocyanurate, the triester of beta-(4-hydroxy-3,5-ditert.butylphenyl) propionic acid with 1,3,4-tris-(2-hydroxyethyl)-5-triazinyl-2,4,6 (1H,3H,5H) -trione, bis (3,3-bis- (4′-hydroxy-3-tert.butylphenyl)-butyric acid) glycol ester, 1,3,5-trimethyl-2,4,6-tris-(3,5-ditert.butyl-4-hydroxy -benzyl) benzene, 2,2′-methylene-bis-(4-methyl-6-tert.butylphenyl) terephthalate, 4,4-methylene-bis-(2,6-ditert.-butylphenol), 4,4′-butylidine-bis-(tert.butylmetacresol), 2,2′-methylene-bis (4-methyl-6-tert.-butyl)-phenol, 1,3,5-tris-(3,5-di-t-butyl-4-hydroxyphenyl)-isocyanurate and 1,1,3,tris- (5-tert.butyl-4-hydroxy-2-methylphenyl)-butane.

Preferred sulphur-containing antioxidative co-stabilizers which may be used include di-tridecyl-3,3-thiodipropionate, distearyl-3,3-thiodipropionate, di-lauryl-3,3-thiodipropionate, methane tetrakis (methylene-3-hexylthiopropionate), methane tetrakis (methylene-3-dodecylthiopropionate) and diotadecyl disulphide.

Preferred phosphorus-containing co-stabilizers which may be used include trinonylphenyl phosphate, 4,9-distearyl-3,5,8,10-tetraoxadiphosphaspiroundecane, tris- (2,4-ditert.butylphenyl) phosphite, trilauryl phosphite, bis(2,6-di-t.butyl-4-methylphenyl)pentaerylthrityl-diphosphite, bis (2,4-di-t.butylphenyl) pentaerythrityl-diphosphite, distearylpentaerythrityl diphosphite and tetrakis(2,4-ditert.butyl phenyl)-4,4′-biphenylene diphosphonite.

Further additives that can be added to polymeric compositions according to the invention include aminoaryl compounds, U.V. stabilisers and antistatic agents, flameproofing agents, softeners, nucleating agents, metal deactivators, biocides, impact modifiers, fillers, pigments and fungicides.

Preferred aminoaryl compounds include N,N′-dinaphthyl-p-phenylene diamine and N,N′-hexamethylene-bis-3-(3,5- ditert.butyl-4-hydroxy phenyl)-propionamide.

Preferred U.V. stabilisers include U.V. absorbers (e.g. 2-(2′-hydroxy- phenyl)- benztriazoles, 2-hydroxybenzophenones, 1,3-bis-(2′-hydroxy- benzoyl-)benzene salicylates, cinnamates and oxalic acid diamides; U.V. quenchers such as benzoates and substituted benzoates; and hindered amine light stabilisers (for example N-unsubstituted, N-alkyl or N-acyl substituted 2,2,6,6-tetra-alkyl piperidine compounds) other than those of the invention.

Preferably a compound of formula XX

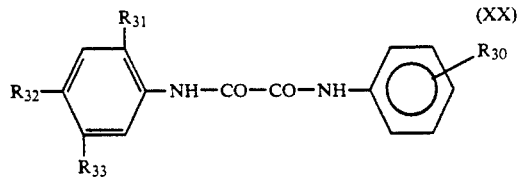

in which

R$_{30}$ is C$_{6-22}$alkyl or C$_{6-22}$alkoxy;

R$_{31}$ and R$_{32}$ independently, are selected from hydrogen, C$_{1-8}$alkyl, C$_{1-12}$alkoxy, C$_{1-12}$alkylthio, phenoxy and phenylthio provided that only one of R$_{31}$ and R$_{32}$ is alkylthio, phenoxy or phenylthio; and R$_{33}$ is hydrogen or C$_{1-8}$alkyl;

is added to a compound of formula I.

The compounds of formula I are especially suitable for use in organic polymer-containing coatings, particularly automotive finishes.

Automotives finishes are generally solutions or dispersion of organic polymers or polymer precursors in organic solvents. The majority are stoving finishes, which require the application of heat, generally above 80° C., on order to harden the finish in an acceptable time once it has been applied to the primer-coated metal surface. The hardening step may be accelerated by the use of an acid catalyst. The effect of this heating may be to accelerate the chemical reaction between polymer precursors in a thermosetting system, or to bring about fusion or particles of a thermoplastic polymer.

Many automotive finishes are metallic finishes, which contain flakes of metal, usually aluminium, in order to provide optical effects due to reflection. Such finishes are often two-coat finishes, in which a clear top coat finish is applied over a base coat finish containing a single pigment and/or metal flakes. The compounds of formula I can be in the top coat finish or the ground coat finish, preferably the former. Such two-coat metallic finishes have particular need to U.V.-stabilizers in the top coat, since the polymer in this coat is not protected by light-absorbing pigments, and it is subjected to almost double the normal amount of radiation because of reflection of light from the lower metallic layer.

The compounds of formula I are suitable for use as U.V.-stabilizers in a wide range of liquid finishes, for example those based on combinations of melamine-formaldehyde resins with oil-modified polyester resins, polyacrylate resins with added crosslinkers, or saturated polyesters; or on self-crosslinked polyacrylate or polyacrylate resin co-polymerised with styrene.

Further examples are two-component finishes based on an aliphatic or aromatic di-isocyanate and a hydroxy-group-containing polyacrylate, polyester or polyether resin. These polyurethane 2-component finishes are preferably hardened at 60° to 120° C. Thermoplastic polyacrylate resins may also be used, the latter being particularly useful in metallic finishes, as are also polyacrylate resins with added crosslinkers in combination with melamine-formaldehyde resins etherified with butanol and, further, hydroxy-group-containing polyacrylate resins are described in U.S. Pat. No. 3,062,753, the contents of which are incorporated herein by reference.

The compounds of formula I are particularly useful in acid catalyzed stoving finishes particularly in the top coat of two layer metallic finishes.

The compounds of formula I may be added to the finish at any stage in its manufacture, and may be added in solid form or in solution, preferably in the form of a liquid concentrate in a suitable solvent or in the form of a dispersion in water or organic liquid.

In practice the compounds of formula I are added to a finish as a solution in organic solvent (as a liquid finish) in which the binder material is between 35% (low solid finishes) and 70% by weight (high solid finishes). The binder material of the finish can be in aqueous emulsion or suspension form (as an aqueous finish) in which the binder material part makes up 20 to 30% by weight. However, the compounds of formula I can be added to known powder finishes.

The compounds of formula I are to be added to the liquid or powder finishes before stoving or hardening. Preferably to the compounds of formula I are used in liquid finishes since it is easy to add exact dosages. It is particularly preferred to use a concentrate (preferably in a hydrocarbon solvent) containing at least 40% preferably 60 to 80% by weight of the total weight of the concentrate of a compound of formula I to finishes for stoving.

The compounds of the invention can also be used in photopolymeric substrates containing photoinitiators for the photopolymerisation.

The compounds of the invention can also be used to stabilize powder lacquers against the effects of light (as well as other weathering properties), the powder lacquer preferably being based on acrylate resin and in particular for use in 2 layer metallic lacquers.

The compounds of the invention may also be incorporated in plastics material to stabilize such material against the effects of light (and other weathering properties). Polypropylene made by any process, preferably by the "spheripol" process may also be stabilized by the products of the invention, as can polyethylene, especially High Density Polyethylene (HDPE), Low Density Polyethylene (LDPE), Medium Density Polyethylene (MDPE) and Linear Low Density Polyethylene (LLDPE).

For the avoidance of doubt, in the Examples triacetone diamine (in Example 1) is 4-amino 2,2,6,6, tetramethylpiperidine:

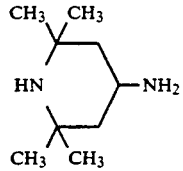

O- phenetidin- monoethyl ester oxanilide is of the formula

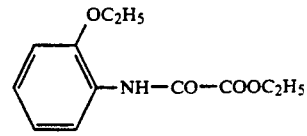

The invention will now be illustrated by the following Examples in which all parts and percentages are by weight and all temperatures are in ° C.

EXAMPLE 1

47.4 g (0.2M) of o-phenetidin-monoethyl ester exalanilide is warmed to 122° in 50 ml of xylene. 31.2 g (0.2M) of triacetone - diamine are added dropwise over 15 minutes to the clear solution. The mixture is stirred at 128° C. for a further 3 hours and alcohol is split off. The clear light yellow solution is cooled, the mixture is diluted with hexane the precipitate is filtered off and then the precipitate is dried under vacuum at 50° C. for 2 hours. The resulting yield is 62.4 g of the compound of formula 1a

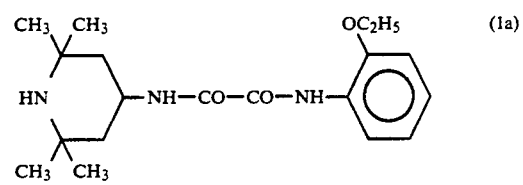

which is 90% of theory. The product has a melting point of 108° to 110° C.

EXAMPLE 2

12.8 g (0.05M) of the compound of formula 2b

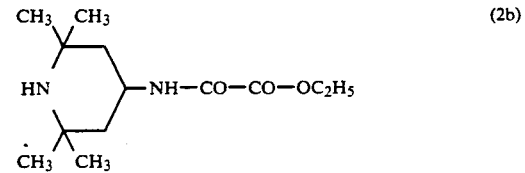

and 5 g (0.0025M) of 4 4'-diaminodiphenylether are stirred together in a bath at 185° for 7 hours and a yellow melt results. After cooling to 110°, the product is diluted with 50 mls toluene, filtered off and washed with water and methanol and the white product is vacuum dried.

A product of formula 2a

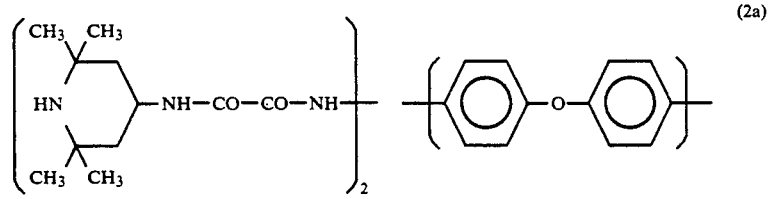

(60% of theory) results having a melting point of 174°–180°.

EXAMPLE 3

12.8 g (0.05M) of the product of formula 2b and 8.6 (0.05M) of 4-amino biphenyl are stirred together over 5 hours in a bath of 185° and a thick beige mass results. This is cooled to 80°, 30 mls of xylene are added and the mass is diluted with 30 mls of methanol and the precipitate is then filtered off. It is washed with methanol and water and the product is vacuum dried at 80° 15 g of a compound of formula 3a

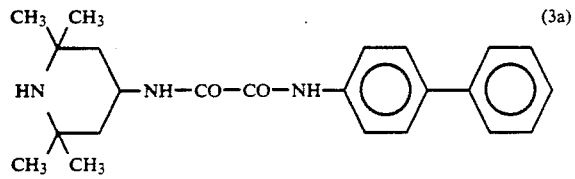
(3a)

which is 79% of theory, results having a melting point of 243°-244° and is clear and colourless.

EXAMPLES 4 TO 16

Starting from appropriate reactants, compounds of the formula

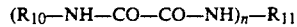

where $R_{10}$ and $R_{11}$ are given in the Table below and where $n=1$ in all examples except Example 13 where $n=2$ can be made according to the method of Example 1.

TABLE

| Example No. | $R_{10}$ | $R_{11}$ | Melting point | λ max. |
|---|---|---|---|---|
| 4 | (2,2,6,6-tetramethylpiperidin-4-yl, HN-) | 2,3-dimethylphenyl | 171–173 | 283 nm |
| 5 | " | 4-phenoxyphenyl | 193–194 | 283 nm |
| 6 | " | 4-N(CH₃)₂-phenyl | 224–225 | 322 nm |
| 7 | " | 2-C₂H₅-phenyl | 215–216 | 280 nm |
| 8 | " | 2-OC₁₂H₂₅-phenyl | | 300 nm |
| 9 | " | 2,5-dimethylphenyl | 240–241 | 283 nm |
| 10 | " | 2,4-dimethylphenyl | 225–226 | 283 nm |

TABLE-continued

| Example No. | $R_{10}$ | $R_{11}$ | Melting point | λ max. |
|---|---|---|---|---|
| 11 | " | 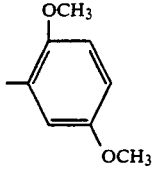 | 147–148 | 319 nm |
| 12 | " | 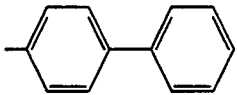 | 243–244 | 295 nm |
| 13 | " | 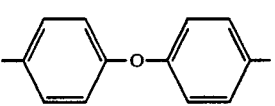 | 174–180 | 290 nm |
| 14 | " | 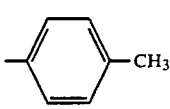 | 198–200 | 283 nm |
| 15 | 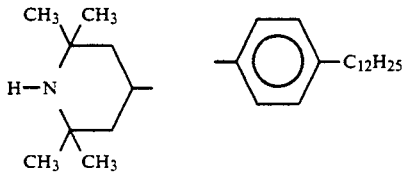 | —⟨◯⟩—C$_{12}$H$_{25}$ | resin | 283 nm |

APPLICATION EXAMPLE A

A clear finish of
80 Parts of Viacryl SC 344 (a 50% solution of an acryl resin from Vianova),
13.9 Parts of Maprenal MF 80 (a 72% solution of a melamine resin from Hoechst) and
4.1 Parts of Byketol OK (from Byk-Malinckrodt)
is added to 2 parts of a compound of formula 1a (described in Example 1).

After 1 minute the light stabiliser material so formed is dissolved in a finish. The finish is applied conventionally (according to the known 2 layer procedure) to a metallic or single piment finish whilst still wet by spraying to form a layer having at thickness of 30 to 40 μm. The resulting coating is then hardened at 140° for 30 minutes. The coating shows very good resistance to U.V. light and weathering.

APPLICATION EXAMPLE B

A clear finish of
29.5 Part of Setalux C-1502 XX-60 (a 60% solution of an acryl resin from Synthese B.V.),
39.2 Part of Setalux C-1382 BX-45 (a 45% solution of an acryl resin from Synthese B.V.),
21.4 Parts of Setamine US-138 BB-70 (a 70% solution of a melamine resin from Synthese B.V.),
2.5 Parts of Baysilonil [2% solution in Xylene) from Bayer] and
7.4 Parts of Depanol Y (a solvent from Hoechst)
is stirred together with 2.5 parts of a compound of formula 1a (described in Example 1) and 2 parts of an acid catalyst derived from phosphoric acid (Type: Catalyst 269-9 from American Cyanamid) to form a homogeneous mixture.

The finish is applied conventionally (according to known 2 layer procedure) to a metallic or single pigment finish whilst both are still wet by spraying to form a layer having a thickness of 30 to 40 μm. The resulting coating is then hardened at 110° for 20 minutes. The coating shows very good resistance to U.V. light and weathering.

APPLICATION EXAMPLE C

A clear finish of
75 Parts Macrynal SH 510 N (a hydroxy containing acryl resin from Bayer)
2 Parts of Baysilon-oil A [(1% solution in xylene) from Bayer]
0.3 Parts of dibutyl zinc dilaurate
0.35 Parts of diethanolamine
5.0 Parts of ethyl glycol acetate
5.0 Parts of Solvesso 100
6.0 Parts of Xylene and
6.36 Parts of butyl acetate are added to 2.5 parts of a compound of formula 1a (described in Example 1) and.30 parts of Desmodur N 75 (from Bayer).

The homogenous mixture so formed is applied conventionally (according to the known 2 layer procedure) to a metallic or single pigment finish whilst both are still wet by spraying to form a layer having a thickness of 30 to 40 um and the resulting coating is hardened over 20 minutes at 80° to 90°. The resulting 2K-PUR coating shows a good resistance to U.V. light and weathering.

APPLICATION EXAMPLE D

A single white pigmented finish of 14.30 Parts of Setamine US-132 BB70 (a 70% solution of a melamine resin from Synthese);
57.15 Parts of Setal 84 W-70 (a 70% solution of an alkyd resin from Synthese);
7.70 Parts of n-butanol;
1.85 Parts of butyl glycol acetate; and
9.50 Parts of titanium dioxide (Rutil type)
is added with 1.38 parts of the product of formula 1a (see Example 1).

The finish is conventionally applied to a grounded steel metal to which a filler of layer thickness 20 to 30 μm has been annealed, by spraying and after standing for 30 minutes at room temperature the steel metal surface is annealed at 120° C. for 30 minutes. The resulting coating shows very good resistance to U.V. light and weathering.

APPLICATION EXAMPLE E

Polycarbonate based on bisphenol A and having a relative viscosity of $\eta_{r.1} = 1.274$ is mixed with 0.5% by weight of the compound 1a of Example 1 at about 280° C. and homogenized. The homogenous mixture is then worked up into test rods 4 mm in thickness at 330° C. These test rods are used to measure the percentage light transmission value at 420 nm immediate after incorporation of the compound 1a of Example 1, after tempering and after weathering in a weatherometer. The resultant polymers have good stability to light.

APPLICATION EXAMPLE F 100 parts of polypropylene powder (melt index 1.5 g/10 minutes, 230° C., 2,160 g load) are mixed in a drum mixer with 0.1 part of pentaerythritol tetrakis-[3-(3',5'-ditertiary butyl-4-hydroxyphenyl)-propionate] and 0.15 parts of the compound 1a of Example 1. The mixture is extruded in an extruder at 200°–220° C. and granulated. The resulting granules are processed in the conventional manner by means of an extruder with a sheet die to give films, which are cut into tapes, which are then stretched to six times their length at elevated temperature. The gauge of these tapes is 700–900 denier, their width is 4 mm and their tear strength is 5.5–6.5 g/denier. These tapes are exposed in a Xenotest 1200. At regular intervals samples are subjected to a stress-elongation test and a progressive fall in the tear strength results as the exposure time increases. The exposure time which elapses before the tear strength has fallen to half of its initial value is lengthened by the action of the light stabilizers.

APPLICATION EXAMPLE G 2 g of the compound 1a of Example 1 and 1 g of 2,6-di-t-butyl-p-cresol (antioxidant) are thoroughly mixed with 1,000 g of polypropylene of melt index 3.2 (Moplen C, a product of Societa Montedison) and 1 g of calcium stearate.

The mixture obtained is then extruded at a temperature of 200°–230° C. and converted to granules, from which tapes having a thickness of 40 μm and a width of 3 mm are produced. The working conditions are as follows;

| Extruder temperature | 230–240° C. |
|---|---|
| Head temperature | 240° C. |
| Stretch ratio | 1:6 |

The tapes obtained are exposed in a Weather-Ometer 65 WR (ASTM G27-70) with the temperature of the black panel at 63° C. Samples are taken periodically and the residual tensile strength of these is measured by means of a tensometer at constant speed: the exposure time required to halve the initial tensile strength ($T_{50}$) is then determined.

The resulting polymer has good stability to light.

APPLICATION EXAMPLE H 2 of the compound 1a of Example 1 is thoroughly mixed with 1,000 g of hight density polyethylene of melt index 0.32 (Moplen RO ZB-5000, a product of Societa Montedison), 0.5 g of di-n-octadeeyl 3-(3,5-di-t-butyl-4-hydroxyphenyl)-propionate (antioxidant) and 1 g of calcium stearate.

The mixture obtained is then extruded at a temperature of 190° C. and converted to granules from which discs of thickness 0.2 mm are produced by compression moulding at 200° C. and the increase in carbonyl groups (ΔCO) is checked periodically, employing non-exposed samples to compensate for the initial absorption of the polymer. The polymers have a good stability to light.

APPLICATION EXAMPLE I 100 parts of polypropylene powder (Moplen, fibre grade, Montedison) are homogenized with 0.2 parts of octadecyl β-(3,5-di-tert.-butyl-4-hydroxyphenyl)-propionate, 0.1 part of calcium stearate and 0.25 part of the compound 1a of Example 1 for 10 minutes in a Brabender plastograph at 200° C. The mass thus obtained is removed from the kneader as rapidly as possible and pressed to a 2–3 mm thick sheet in a toggle press. A piece of the resulting crude moulding is cut out and pressed between two high-gloss hard aluminium foils with a hydraulic laboratory press at 260° C. for 6 minutes to give a 0.1 mm thick film, which is immediately chilled in cold water. Sections of this film are then stamped out and exposed in a Xenotest 1200.

In Application Examples A to I instead of the compound of formula 1a, the same amount of the product of any one Examples 2 to 15 can be used.

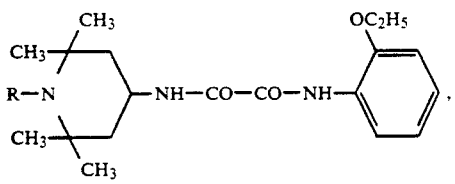
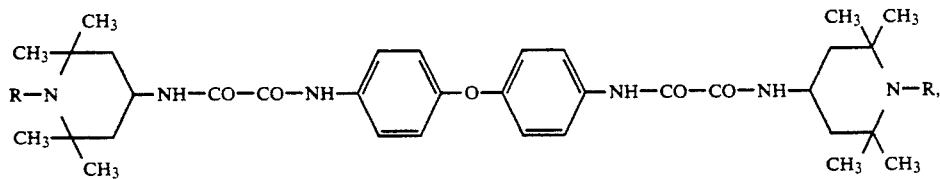
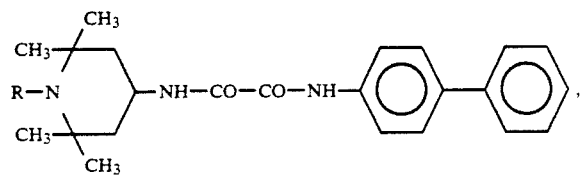
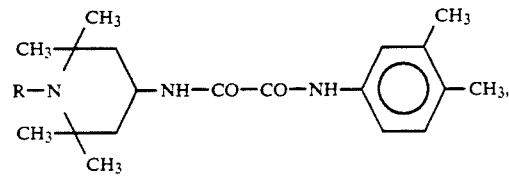
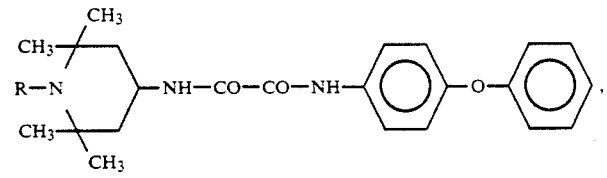
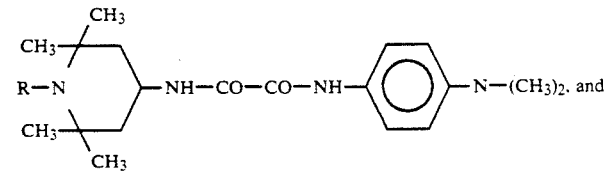
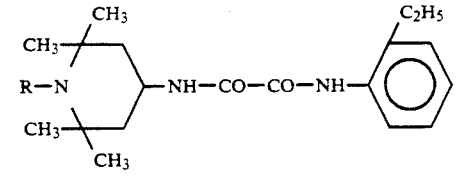
8. A compound according to claim 1, selected from the group consisting of:
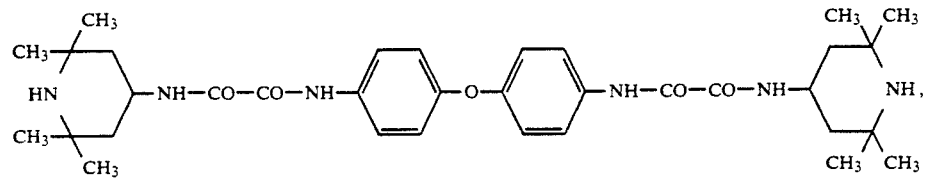

-continued
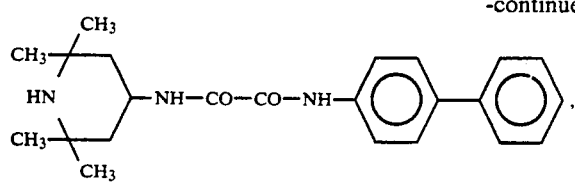
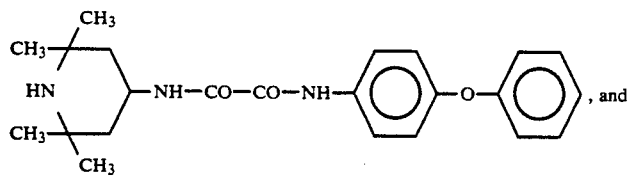, and
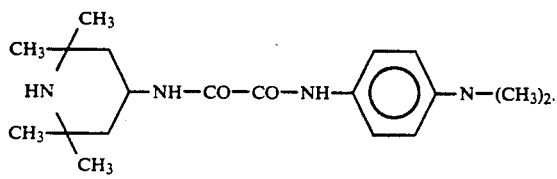

What is claimed is:

1. A compound of formula I

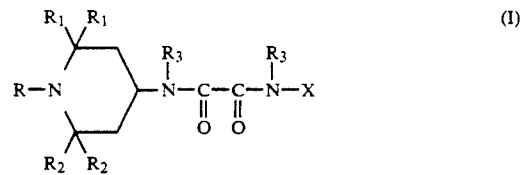

in which

R is hydrogen; oxygen; —OH; $C_{1-8}$alkyl; —O—$C_{1-8}$alkyl; —O—OC—$C_{1-8}$ alkyl; —O—CO—phenyl or —COR$_5$;

where

R$_5$ is —C(R$_3$)=CH$_2$, $C_{1-6}$alkyl, phenyl, —CO—phenyl, —NR$_7$R$_8$, —C$_2$—C$_6$H$_5$, —CO—OC$_{1-12}$ alkyl or —COOH; R$_7$ is hydrogen, $C_{1-12}$ alkyl, $C_{5-6}$ cycloalkyl, phenyl, phenyl-$C_{1-4}$alkyl or $C_{1-12}$alkyl-phenyl and R$_8$ is $C_{1-12}$alkyl or hydrogen, each R$_1$ independently, is —CH$_3$ or —CH$_2$($C_{1-4}$alkyl) or both groups R$_1$ form a group —(CH$_2$)$_5$—;

each R$_2$, independently, is —CH$_3$ or —CH$_2$($C_{1-4}$ alkyl) or both groups R$_2$ form a group—(CH$_2$)$_5$—;

each R$_3$ independently, is hydrogen or $C_{1-4}$ alkyl; and

X is a group of formula α, β, γ, δ

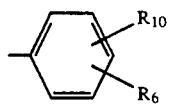

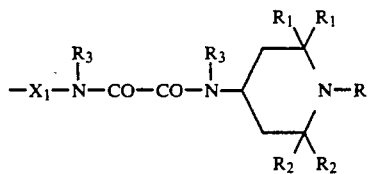

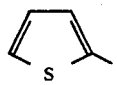

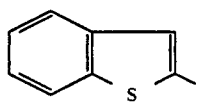

where
either $R_{10}$ is

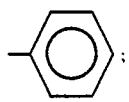

$C_{1-22}$alkyl; $C_{2-22}$alkenyl;

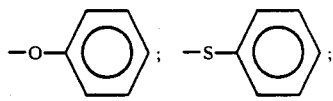

—$N(C_{1-4}alkyl)_2$; —$NH(C_{1-4}alkyl)$ or halogen, and $R_6$ is hydrogen, halogen, $C_{1-8}$alkyl or $C_{2-8}$alkenyl or $R_{10}$ is $C_{1-22}$alkoxy and $R_6$ is hydrogen, $C_{1-8}$alkyl or $C_{1-8}$alkoxy; provided that when $R_{10}$ is alkyl or alkoxy, $R_6$ is hydrogen, R is —OH, —O—$C_{1-8}$alkyl, —O—OC—$C_{1-8}$alkyl, —O—CO— phenyl, or —$COR_5$; where $R_5$ is $NR_7R_8$, —CO—phenyl, —$CH_2$—$C_6H_5$, —CO—$OC_{5-12}$alkyl or —COOH; and
$X_1$ is (α) 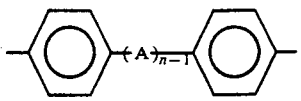

where n is 1 or 2 and A is —S— or —O—.

2. A compound according to claim 1 in which R is R' where R' is hydrogen, $C_{1-4}$alkyl, O—$C_{1-4}$alkyl or —CO—$R_5'$ where $R_5'$ is —$CH=CH_2$, $C_{1-4}$alkyl or —CO—O—$C_{1-4}$alkyl.

3. A compound according to claim 1 in which X is X' where X' is a group of formula α' or β'

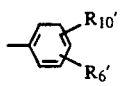

(β) 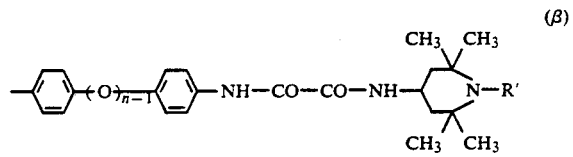

where
either $R_{10}'$ is selected from $C_{1-4}$alkyl, $C_{2-4}$alkenyl, —$N[C_{1-4}alkyl]_2$; —$NH(C_{1-4}alkyl)$ and phenyl; and $R_6'$ is hydrogen or methyl or
$R_{10}'$ is $C_{1-4}$alkoxy and $R_6'$ is hydrogen, $C_{1-4}$alkyl or $C_{1-4}$alkoxy provided that when $R_{10}$ is alkyl or alkoxy, $R_6$ is hydrogen, R is —OH, —O—$C_{1-8}$alkyl, —O—CO—$C_{1-8}$alkyl, —O—CO—phenyl, or —$COR_5$; where $R_5$ is $NR_7R_8$, —CO—phenyl, —$CH_2$—$C_6H_5$, —CO—$OC_{5-12}$alkyl or —COOH; and $\eta = 1$ or 2.

4. A compound according to claim 1 in which each $R_1$ and each $R_2$ is methyl.

5. A compound according to claim 1 in which $R_3$ is $R_3'$ where $R_3'$ is —$CH_3$ or hydrogen.

6. A compound according to claim 1 in which X is X' wherein
X' is a group according to formula α' or β';

(α') 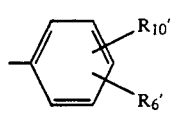

(β') 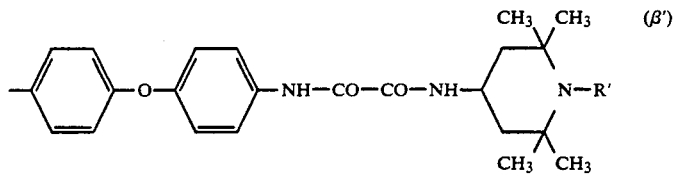

where
either $R_{10}'$ is selected from $C_{1-4}$alkyl, $C_{2-4}$alkenyl, —$N(C_{1-4}alkyl)_2$; —$NH(C_{1-4}alkyl)$ and phenyl; and $R_6'$ is hydrogen or methyl;
or $R_{10}'$ is $C_{1-4}$alkoxy and $R_6'$ is hydrogen, $C_{1-4}$alkyl or $C_{1-4}$alkoxy, provided that when $R_{10}'$ is alkoxy and R is —$COR_5$, then $R_6'$ is not hydrogen, and n is 1 or 2.

7. A compound according to claim 1 selected from the group consisting of